United States Patent [19]

Eirich et al.

[11] 4,186,592
[45] Feb. 5, 1980

[54] METHOD OF MEASURING THE MOISTURE CONTENT IN FLOWABLE MATERIALS AND APPARATUS FOR CARRYING OUT THE METHOD

[76] Inventors: Hubert Eirich, Erster Sandweg 16, 6969 Hardheim; Walter Eirich, Spessartweg 18, 6969 Hardheim; Paul Eirich, Bahnhofstrasse 11 6969 Hardheim; Josef Hasenhündl, 6965 Ahorn-Berolzheim, Eubigheimdr-str.840; Adolf Spengler, Haagstrasse 6, 6987 Kulsheim, all of Fed. Rep. of Germany

[21] Appl. No.: 877,673

[22] Filed: Feb. 14, 1978

[30] Foreign Application Priority Data

Mar. 19, 1977 [DE] Fed. Rep. of Germany ....... 2712210

[51] Int. Cl.² ............................................. G01N 33/38
[52] U.S. Cl. ............................................. 73/73; 366/17
[58] Field of Search ................ 73/73; 366/17, 40, 151

[56] References Cited

U.S. PATENT DOCUMENTS

| | | | |
|---|---|---|---|
| 2,825,946 | 3/1958 | Dietert et al. | 366/17 |
| 2,852,740 | 9/1958 | Posey et al. | 73/73 |
| 2,863,191 | 12/1958 | Dietert et al. | 366/17 |
| 3,631,337 | 12/1971 | MacKinney | 366/17 |
| 3,791,214 | 2/1974 | Keith | 73/362 AR |
| 4,042,497 | 8/1977 | Maltby | 73/73 |

FOREIGN PATENT DOCUMENTS

1361885  4/1964  France ..................................... 366/17

*Primary Examiner*—Anthony V. Ciarlante
*Attorney, Agent, or Firm*—Biebel, French & Nauman

[57] ABSTRACT

A method and apparatus for measuring water content of flowable mixtures such as casting sand, concrete, or chemical mixtures. The mixture is agitated in a mixing tray (10), then a moisture sensing measuring probe (7) is inserted into the mix for taking a measurement. The probe is then withdrawn from the mix and cleaned, as by brushing, stripping, blasting with air, or spraying with liquid. A temperature sensor (8) may also be inserted into the mix with the measuring probe. The probe is mounted in a lifting unit (5) which normally holds the probe in a cooling and cleaning casing (6) out of the mix. The unit can also locate the probe at different selected levels within the mix.

11 Claims, 1 Drawing Figure

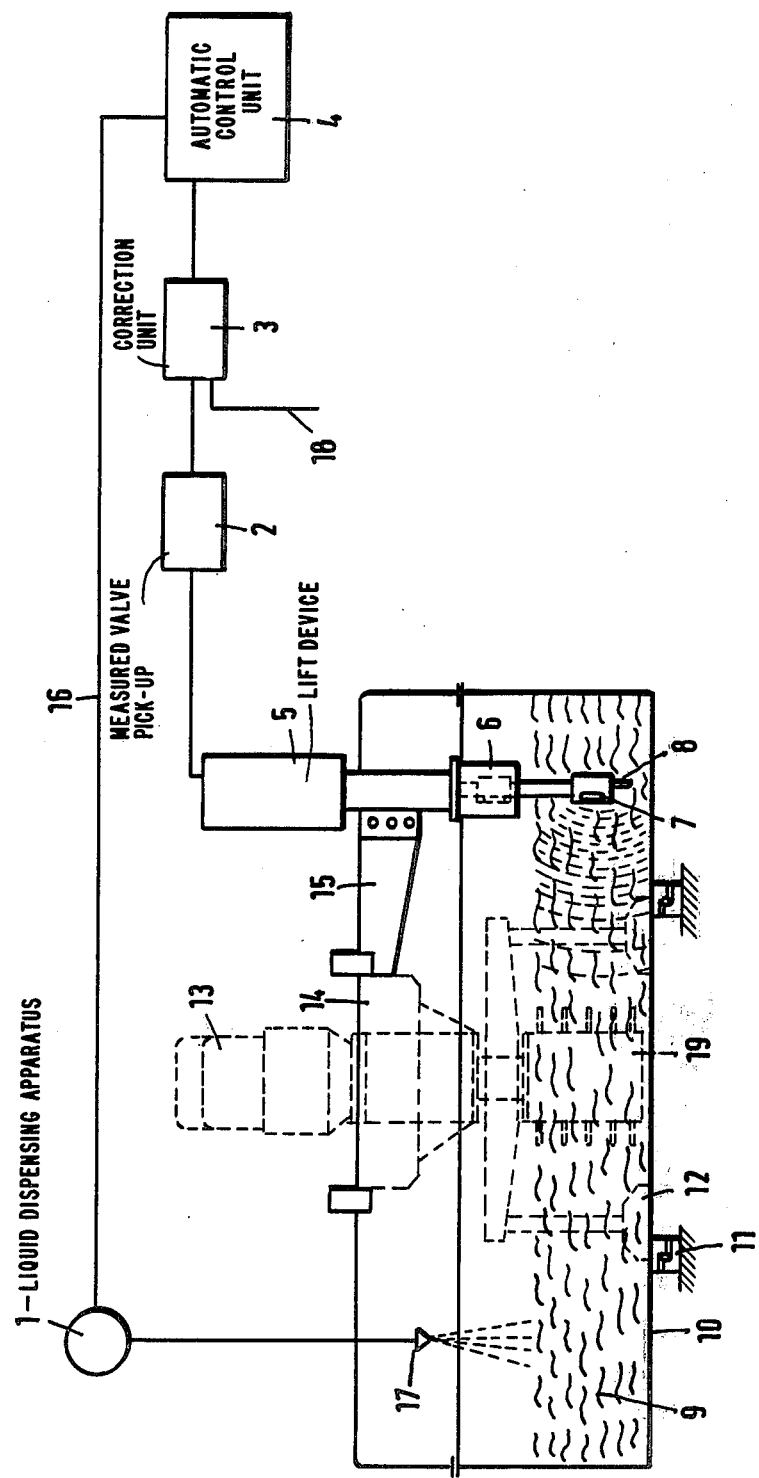

METHOD OF MEASURING THE MOISTURE CONTENT IN FLOWABLE MATERIALS AND APPARATUS FOR CARRYING OUT THE METHOD

BACKGROUND OF THE INVENTION

The invention relates to a method of and an apparatus for measuring the water content of flowable materials, e.g. casting sand, concrete admixtures or chemical mixtures, by determining a physical quantity or property of the moist material in contact with a measuring probe and by converting this physical quantity into a measurable electrical signal, the measuring probe being submerged in the stationary or flowing material.

Various methods and apparatuses for measuring the moisture content are known, and during recent years three methods, suitable for automatic operation, have crystallized out, namely, the conductivity method, the nuclear physical method and the di-electrical method. The method and apparatus for measuring moisture content in accordance with the invention are suitable for use in various measuring systems including the capacitive system. In the following, the method will be described in connection with the determination of the dielectric constants and the high-frequency attenuation of the measured material in the short-wave range to enable an illustrative specific method to be selected from several possible methods, without limiting the invention to the selected one.

In the production of concrete the measurement of the moisture content for example is of decisive importance, not least as regards the controlled addition of moisture and therefore as regards determination of the water-cement ratio. In many cases it is not sufficient, for the purpose of maintaining particular material properties, simply to accept a mean value based on the range over which the moisture content varies, and it is particularly advisable in automated operations to measure the actual moisture content of the materials on a continuous basis and to correct the amounts of added components accordingly.

In measuring the electrical conductivity of the material to be processed two or more electrodes are used in known methods, and the moisture content of the mixture disposed between the electrodes is determined by measuring the change in resistance. Although such conductivity measuring instruments are not expensive, the value indicated by them is disadvantageously dependent upon impurities in the material and upon temperature.

It is also known to measure the dielectric constants in conjunction with the high-frequency attenuation of a moist medium, in contact with the measuring probe, in the short-wave range.

Most of the known methods are limited to carrying out measurements in containers, silos or conveyor means, e.g. on conveyor belts. However, the dielectric is greatly altered by the degree of compacting of the material and by differences in, or absence of, homogeneity in the measuring medium. Furthermore, moisture-content values, measured in preliminary containers or trucks, are intended to be used for correcting the moisture content by adding a suitable quantity of water to obtain the required value, this operation being carried out in a following machine for preparing the material. However, when measurements are carried out in stationary containers, there arises the problem that only part of the amount of the material that is used for preparing each charge is subjected to the measurement. Since, however, many bulk materials, such as for example casting sand, exhibit considerable variations in moisture content, the determination of a value relating to only part of the material just does not provide reliable information regarding the average moisture-content of the entire quantity. Even if the measuring probe is submerged in material passing along on conveyor belts, considerable variations in the measured values are observed which are caused either by the material having caked up in a silo discharge duct or by uneven depth of layer of material on the conveyor belt. Fluctuations in mositure content can also be caused by lumping and the like.

In the case of measurements in media having higher temperatures, it has for many years been impossible, by electronic methods, to effect temperature-compensation in the oscillatory circuit of the probe, so that here again unreliable measurements have occurred. However, since it is important with many mixtures to be able to determine the temperature of the mixture for the purpose of ascertaining the required amount of moisture, temperature sensors have also been provided on conveyor belts at positions considerably in advance of, or to the rear of, the moisture-content measuring probe. Temperature sensors are generally of fairly considerable mass in order to reduce wear and tendency to breakdown. Then however not only does inertia occur in the measuring system, but the temperature measurement is also falsified as a result of the fact that the measuring sensor itself requires a long time to reach the high temperature of the material on which the measurements are being carried out, since after each measurement it does not cool down again to the initial temperature.

A particularly disadvantageous feature associated with the known moisture-content measuring methods and apparatuses is the danger of substances adhering to the probe and of its becoming contaminated, particularly after repeated and/or automatic use. This difficulty is repeatedly observed in the case of sticky dirty materials.

SUMMARY OF THE INVENTION

The object of the present invention is therefore to provide a method of measuring moisture content of the initially stated kind, and an apparatus for carrying out the method, which method enables moisture-content values, representative of the entire quantity of material, to be obtained, even when the measuring probe has been repeatedly used or when the system is operated on an automatic basis, as well as when the material concerned is sticky and dirty and possibly at a fairly high temperature.

In the method of the invention, this object is achieved in that the measuring probe is moved from a protected position and submerged in the material, rendered substantially uniform in a vessel, by relative movement between the probe and the material, the probe, after completion of the measurement, being withdrawn from the stream of material, cleaned and/or cooled, and returned to the protected position. As initially stated, the new method is also suitable for use in resistance measurements, capacitive measurements, in the determination of electrical constants and the like. It greatly improves the known system, since if, in accordance with the invention, the measuring probe is introduced into the material, that is to be subjected to the measurements, only after the material has been rendered uniform, then variations due to the differing inherent moistness in some of the components can be excluded in a reliable manner, and the physical amount of the actual moisture content or the dielectric constant is distributed in a completely uniform manner, the same applying as regards conductivity and other physical amounts. Advantage also accrues from the use of a vessel in which the material is rendered uniform since then a substantially constant depth of layer of the material to be subjected to the measurements is provided. Furthermore, due to the fact that the material has been previously rendered uniform, the known uncertainties in the measurements, resulting from lack of uniformity and differing degrees of compacting, do not occur.

The method of the invention is best carried out in a mixing machine, for which reason, in a preferred embodiment, the vessel is a forced-drive mixer having a rotating mixing tray. However, the invention can also be used in other equipment such as for example a moulding-sand cooler, a machine for breaking up lumped material on a batch-wise basis, and the like. For purposes of illustration only, the following refers to a forced-drive mixer wherein the rotating mixing tray moves the medium past the measuring probe which is stationary, for example, so as to obtain the relative movement between probe and material. Thus, by means of the new method, the moisture content is determined in a free-standing quantity of material that has previously been rendered uniform, and the amount of extra water to be added later can then be precisely determined.

To prevent the mixed material, which is usually moist and contains a binding agent, from adhering in increasing amounts to the measuring probe when the latter is in contact with the material as a result of repeated submersion of the probe in the material and its withdrawal therefrom during the course of the treatment, and thus to avoid incorrect signals, not only can the probe be withdrawn into a protected position in which it is largely protected against wear and contamination, but upon being withdrawn from the mixed material following the measuring process, the probe is cleaned by being passed over a stripping brush for example, and/or by being blasted with a compressed-air jet or sprayed with water-jet.

With many mixed materials it is important, for the purpose of determining the required quantity of moisture, to ascertain, beforehand, the temperature of the material. In the method of the invention, temperature sensors used for this purpose are advantageously cooled down again to the initial temperature after the measurement has been carried out and the probe has been returned to the protected position. The measuring head used can be withdrawn into a casing and therein blasted with compressed air so that the probe can be brought again to the initial temperature after each measurement. Therefore, according to the invention, it is advantageous if the cleaning of the measuring probe is carried out by brushing, stripping, or blasting with compressed air or spraying with a liquid. For example, the excess pressure, occurring in the protective casing as a result of blasting with compressed air, can also prevent dust from the mixing chamber from penetrating into the casing and contaminating the measuring probe.

Because of the effect of temperature on the moisture-content measurement that has been mentioned several times above, it is advantageous if, in accordance with the invention, temperature measurement is also carried out during measurement of the moisture content for example. Also, a further preferred form of the method is characterized in that the measuring probe is heated to a certain temperature, corresponding to the stream of material, prior to each measuring operation. This can be done by, for example, blowing warm air into the compartment, in which the measuring probe is present at least temporarily, so as to raise the probe to a constant higher temperature and to eliminate any results that may be falsified by the effects of temperature.

Advantageously, the method is such that the measuring probe is rotated or oscillated in the material. The measuring probe is generally kept stationary in the above-described forced-drive mixers since the material is moved relatively to the stationary measuring probe by the positively driven mixing tray. In other receptacles having for example stationary containers, the method of the invention can likewise be used with advantage if the measuring probe is moved.

The apparatus for carrying out the method, particularly when a mixing machine is used, is characterized in that the measuring probe can be lowered on a lifting device from a protective casing, secured above the layer of material, into this layer and can be lifted therefrom back into the protective casing, and in that cleaning means and/or cooling and heating means are mounted on the protective casing. The advantageous effects, described above in connection with the method of the invention, also apply as regards the apparatus.

In particular, it is preferred that the apparatus of the invention be so designed that the cleaning means comprise strippers and/or brushes and/or nozzles for spraying a pressurized fluid. Cleaning can therefore be carried out by mechanical contact with a stripper or a brush, and it can likewise be advantageously achieved by blowing gases, particularly air, on to the probe or spraying it with liquids, preferably water.

Whereas a preferred embodiment of the invention is characterized in that a temperature sensor is secured to the measuring probe, it is also possible for the measuring probe itself to be designed to carry out, at choice, the measurement of more than one physical amount such as for example water-content and temperature. Whereas it is known to use the measuring probe for determining the moisture-content and to plunge a temperature sensor into the material separately and at a distance from the measuring probe, it is thus possible, in accordance with the invention, to secure the temperature sensor to the measuring probe or for the measuring probe to be of such internal design that it is able to carry out different measurements, i.e. measurements of different kinds.

It is particularly advantageous if the measuring probe is submerged in the vessel, i.e. in the mixing tray for example, at a position in which the strongest possible flow of material occurs, so that a large portion of the material, of which the moisture-content is to be measured, is contacted during the measuring time. In the case of the majority of known tray-type mixers, this zone is at the periphery of the tray where the greatest peripheral speed obtains. On the other hand, in arrangements that do not promote flow, the measuring probe can be rotated or oscillated when in the submerged position so as to move into contact with the greatest possible quantity of material. In a special form of mixer having a fixed tray and rotating mixing tools, the apparatus of the invention comprising the measuring probe, and thus the method of the invention can be advantageously used if the lifting means is secured to and rotates with a rotating tool system. In this type of mixer the entire surface of the tray is swept by mixing tools so that a fixed probe cannot be introduced from above into the material at any position. It is therefore advantageous if the probe is arranged on an already present or an additionally fitted arm of the mixing system and is rotated with the mixing tool. The measuring probe can then be connected electrically by means of sliding contact rings for example.

The measuring apparatus in accordance with the invention can be used not only for mixers operating on a batch-wise basis, but for continuously driven mixers. In the latter case, a differing state of mix occurs in the various zones of the mixer between its inlet and its outlet. It would therefore be desirable to be able to insert the measuring probe into the layer of mixed material over differing depths. According to the invention therefore, the measuring probe and/or the temperature sensor are or is adjustable as regards their or its position above the base of the mixing tray. For example, the measuring probe can be disposed less deeply in the vicinity of the inlet and more deeply near the outlet. Thus, moisture-content measurements can be advantageously carried out in different zone, and the output signals based on these measurements can then be used to regulate the amount of water added.

When the probe is submerged particularly deeply or when particularly heavy bulk materials are to be subjected to measurements, it is advantageous if the probe is not introduced vertically downwards into the layer of mixed material. According to the invention therefore the measuring probe is mounted to be moved at an angle to the mixing tray and is preferably arranged at the periphery of the tray. In this way the mechanical lateral thrusts, which in some instances are very considerable, are taken into account and have no harmful effects. The probe may be inserted into the mixed material at, for example, an angle of 45° and in the direction of flow of the material. The slope and the submersion depth are expediently selected to suit the particular flow of material.

Furthermore, in a further advantageous form of the apparatus in accordance with the invention, a plurality of vessels each having at least one measuring probe are provided, and the probes are connected to a common control instrument and/or to a common computer. It then becomes possible to operate a plurality of mixers on a time-staggered basis and to connect the probes fitted in the mixers to one and the same control instrument. Thus, several mixers having only one control instrument can nevertheless be equipped with an automatic moisture-content measuring device. This also applies in the case where the probe is provided either for temperature measurements only, or for moisture-content measurements, or else for both types of measurement. The probe may be submerged in the material several times during one mixing operation, and, after each stage of the method, it can be used for example for determining a succession of moisture-content and/or temperature values. If the probe is connected to an automatic computer, the values determined can be immediately used for ascertaining the required amount of water to be added or for ascertaining cooling times or the like.

Further advantages, features and possible uses of the present invention will be seen from the attached single drawing which illustrates an apparatus of the invention provided on a forced-drive mixer.

Mounted for rotation on ball-bearings 11 is a mixing tray 10, the drive means for which are not illustrated however since they do not form part of the subject-matter of the invention. The tray 10 may be completely or partially covered as shown diagrammatically. Mixing tools 12 which are submerged in the material 9 to be mixed are driven by a motor 13 shown in broken lines. The depth of the layer of material 9 to be worked is indicated by short sinusoidal lines, i.e. the material occupies approximately one-half of the depth of the mixing tray 10.

Stays 15 are secured to the mounting 14 of the motor 13, which mounting is shown only diagrammatically. Fitted on the stays is the lifting and lowering unit 5 with a cooling and cleaning casing 6 secured at the bottom thereof. Arranged in this unit i.e. in the casing is a measuring probe 7 which has for example one signal transmitter and which can be moved upwards or downwards in the direction of the axis of rotation of the mixing tool 12. Fitted at the lower end of the measuring probe 7 is a thermometer 8 which is preferably what is known as a seconds thermometer. Electrically connected to the lifting and lowering unit 5 for the measuring probe 7 is a measured-value pick-up 2 which is in turn connected to an automatic control instrument 4 by way of a correction unit 3. A control lead 16 runs from the control unit to the automatic liquid-dispensing apparatus 1 which actuates a liquid-injection nozzle 17. A lead 18 runs from the electronic correction unit 3 either to the temperature sensor 8 and/or to another electronic unit, not illustrated, by means of which other influencing factors are detected and accounted for in the electronic correcting unit 3 when arriving at the measured value.

The mode of operation of the moisture-content measuring apparatus is as follows: The mixed material 9 on which the measurements are to be carried out and which may consist of a plurality of constituents is first loaded into the rotating mixing tray 10. By means of the rotating mixing tools 12 and the rotating mixing tray, which is often also provided with what are known as "swirlers", the material is thoroughly mixed or rendered uniform within a few minutes so that any inherent moisture that may have been present in the components is uniformly distributed throughout the entire material.

The measuring probe 7 is then introduced into the material 9 with the aid of the lifting and lowering unit 5. The measuring probe 7 transmits a specific electromagnetic wave-energy, preferably in the short-wave range, into the homogenized material which is caused to move continuously past the measuring probe 7 by the rotating mixing tray 10. The dynamic and static pressure conditions are thus kept constant.

Change in the wave-energy, which is directly dependent upon the moisture-content of the material, is recorded by the electronic measured-value pick-up 2. The recorded value is then amended by the electronic correcting unit 3 if this is necessary in the light of the temperature recorded by the temperature sensor 8, or is necessitated by other influencing factors. The electronic correction unit 3 is also able to provide corrected values that allow for moisture due to cooling or evaporation occurring over operating lines of different lengths.

The moisture-content value so determined is either processed in the automatic main control unit 4 or is stored until a suitable time. The main control unit then supplies the necessary quantity of liquid through the nozzle 17 with the aid of an automatic liquid-dispensing apparatus 1, so that the required final moisture-content is then present in the mixed material. In addition to the addition of liquid in controlled amounts, it is also possible to add specific quantities of individual constituents for correction purposes. As soon as the measured value has been processed in the main control unit 4, the measuring probe 7 is lifted out of the material 9 and is moved up into the cooling and cleaning casing 6. The probe 7 then reaches the position shown in broken lines in the drawing. If the mixing temperatures are fairly high it is necessary to cool the measuring probe 7 so as to provide a constant starting basis in the oscillatory-circuit electronic system. When sticky and dirty materials are to be worked, it is particularly important to clean the measuring probe e.g. by brushing or stripping or by blasting with compressed air or spraying with a liquid. A further possible way of cleaning the measuring probe would be to rotate it very rapidly by means of a drive provided specially for the purpose, so that adhering material is flung off by centrifugal force.

After the mixing tray 10 is empty, the same moisture-content measuring method is carried out again. In this way it is also possible to carry out a final moisture-content check before emptying the material from the tray 10. With the aid of the temperature sensor 8, which is designed as a seconds thermometer, the temperature of the uniform mixed material can be measured within a few seconds. This value is particularly important in the case of evaporation-cooling systems for the addition of cooling liquids, or for the correction of moisture-content in the case of varying lengths of the path to the processing points.

Practical tests on casting sand at a temperature of 40° to 60° C., and wherein 14 samples were taken per day, showed that the measured moisture-content values varied from each other on average by only 0.08%. This confirms the considerable advantage of the new method and the apparatus for carrying it out.

For carrying out measurements requiring the use of two probes, it would be feasible to introduce the probes into the material along lines parallel to each other.

We claim:

1. A method for measuring the water content of flowable materials, e.g., casting sand, wet concrete or chemical mixtures, in a mixing tray fitted with a mixing tool for mixing said material and being relatively rotatable with regard to said mixing tray, a lifting and lowering unit having a cooling and cleaning casing disposed in stationary position above the level of the surface of flowable material in said mixing tray and vertically movably supporting a moisture sensing probe which is movable between a retracted position wherein said probe is disposed within said cooling and cleaning casing and an extended position wherein said probe is disposed in the flowable material, an automatic liquid dispensing means having a liquid injection nozzle disposed for injecting liquid into said flowable material and control means for receiving signal input from said probe and operating said liquid dispensing means to adjust the liquid content of said flowable material to a predetermined value, comprising the steps of:

(a) agitating a quantity of the material in said mixing tray with said mixing tool to a state of substantially uniform mixture, (b) moving said moisture sensing probe to said extended position disposed in the flowable material, (c) operating said liquid injection nozzle by said control means in accordance with receipt of signals from said moisture sensing probe so as to adjust the moisture content of said flowable material to said predetermined value, (d) retracting said probe to said retracted position in said casing, and (e) cleaning and/or cooling said probe in said retracted position.

2. A method as defined in claim 1, including the additional step of measuring the temperature of the material during the time of the moisture sensing.

3. A method as defined in claim 1, including the additional step of heating the moisture sensing probe to the temperature of the material prior to each moisture sensing reading.

4. A method as defined in any of claims 2, 3, or 1, including the step of moving the moisture sensing probe to different locations in the material.

5. In a mixing apparatus for agitating flowable materials such as casting sand, wet concrete, or chemical mixtures, having a mixing tray in which said flowable material is disposed, a mixing tool disposed in said mixing tray and rotatable relative to said mixing tray for mixing said flowable material to a state of substantially uniform mixture, a moisture measuring probe disposable in said mixture for measuring the moisture content thereof, an automatic liquid dispensing means having a liquid injection nozzle disposed for injecting liquid into said flowable material in said mixing tray, and means associated with said moisture sensing probe for receiving signal input from said probe and operating said liquid dispensing means to inject liquid into said flowable material to adjust the liquid content of said material to a predetermined value, wherein the improvement comprises:

a cooling and cleaning casing disposed above the surface of said flowable material in said mixing tray, and means for moving said moisture sensing probe between a retracted position wherein said probe is disposed in said casing and an operative position wherein said probe is disposed in said flowable material in said mixing tray for measuring the moisture content of said material, and means associated with said casing for cleaning and/or cooling said probe when in said retracted position.

6. A device as defined in claim 5, wherein said cleaning and/or cooling means comprises nozzles for spraying a fluid such as compressed air onto said probe.

7. A device as defined in claim 6, wherein said cleaning and/or cooling means includes brushes for removing parts of the material clinging to said probe after the probe is retracted from the material.

8. A device as defined in claims 6, 7 or 5, wherein said probe is further operative to additionally sense at least the temperature of said material.

9. A device as defined in claims 6, 7 or 5, wherein said lift device includes means for adjusting the immersed position of the probe to different depths.

10. A device as defined in claims 6, 7 or 5, wherein said mixing tray is rotated and said probe is held in a fixed immersed position by said lift device.

11. A device as defined in claims 6, 7 or 5, wherein said lift device is supported by and rotates with said agitator mechanism.

* * * * *